(12) United States Patent
Kim et al.

(10) Patent No.: US 8,580,996 B2
(45) Date of Patent: Nov. 12, 2013

(54) AROMATIC CARBONATE, METHOD OF PREPARING THE SAME, AND POLYCARBONATE PREPARED USING THE SAME

(75) Inventors: Dong Baek Kim, Uiwang-si (KR); Mie Ock Kim, Uiwang-si (KR); Chang Hoon Lee, Uiwang-si (KR)

(73) Assignee: Cheil Industries Inc., Gumi-si (KR)

( * ) Notice: Subject to any disclaimer, the term of this patent is extended or adjusted under 35 U.S.C. 154(b) by 96 days.

(21) Appl. No.: 13/176,005

(22) Filed: Jul. 5, 2011

(65) Prior Publication Data

US 2012/0172573 A1 Jul. 5, 2012

(30) Foreign Application Priority Data

Dec. 31, 2010 (KR) .................. 10-2010-0140049
Mar. 28, 2011 (KR) .................. 10-2011-0027737

(51) Int. Cl.
*C07C 69/96* (2006.01)
(52) U.S. Cl.
USPC ............ 558/277; 528/370; 558/260; 558/274
(58) Field of Classification Search
USPC ......................... 528/370; 558/277, 260, 274
See application file for complete search history.

(56) References Cited

U.S. PATENT DOCUMENTS

2006/0052572 A1  3/2006  Hofacker

FOREIGN PATENT DOCUMENTS

| JP | 05-331108 | * 12/1993 |
| JP | 09-059209 | *  3/1997 |
| JP | 09-59209  |    4/1997 |

OTHER PUBLICATIONS

European Search Report in counterpart European Application No. 11170378.1 dated May 2, 2012, pp. 1-5.
Fu et al., "Two-step synthesis of diphenyl carbonate from dimethyl carbonate and phenol using MoO3/SiO2 catalysts", Journal of Molecular Catalysis A: Chemical, vol. 118, No. 3 (1997) pp. 293-299.

* cited by examiner

*Primary Examiner* — Gregory Listvoyb
(74) *Attorney, Agent, or Firm* — Additon, Higgins, Pendleton & Ashe, P.A.

(57) ABSTRACT

A method of preparing aromatic carbonate from dialkyl carbonate includes reacting an aromatic hydroxyl compound and dialkyl carbonate in the presence of at least one type of samarium-containing catalyst represented by Formula 1, Formula 2, or a combination thereof:

$$SmX_3 \qquad \text{[Formula 1]}$$

wherein each X is the same or different and is independently C1 to C10 alkoxy, C1 to C10 alkyl phenoxy or phenoxy, and

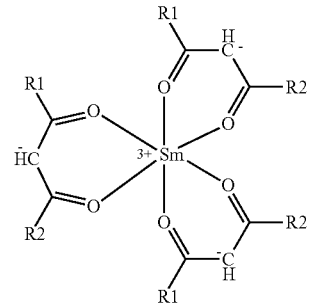

[Formula 2]

wherein R1 and R2 are the same or different and are independently hydrogen or C1 to C6 alkyl.

8 Claims, 1 Drawing Sheet

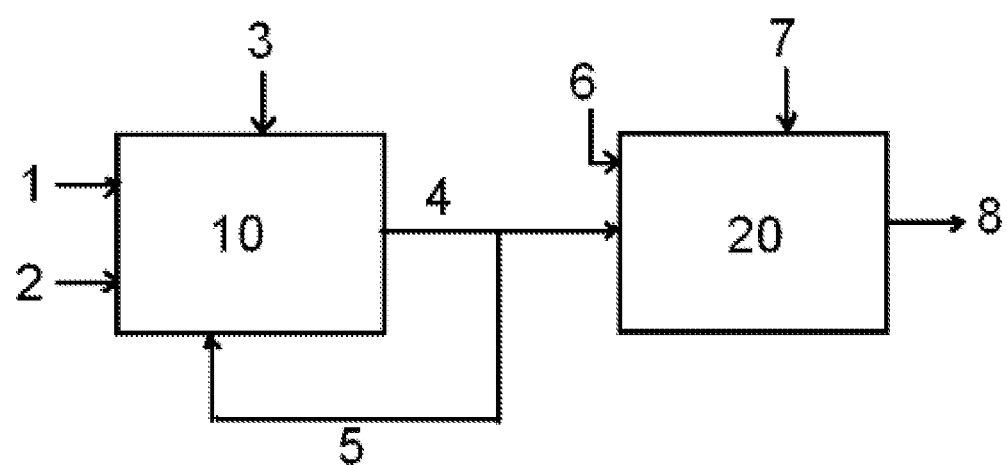

AROMATIC CARBONATE, METHOD OF PREPARING THE SAME, AND POLYCARBONATE PREPARED USING THE SAME

CROSS-REFERENCE TO RELATED APPLICATIONS

This application claims priority under 35 USC Section 119 from Korean Patent Application No. 10-2010-0140049, filed Dec. 31, 2010, and Korean Patent Application No. 10-2011-00027737, filed Mar. 28, 2011, in the Korean Intellectual Property Office, the entire disclosure of each of which is incorporated herein by reference.

FIELD OF THE INVENTION

The present invention relates to an aromatic carbonate, a method of preparing the same, and polycarbonate prepared using the same.

BACKGROUND OF THE INVENTION

Aromatic carbonates are monomers useful for the preparation of polycarbonate and extensive studies have been conducted on developing preparation methods thereof. Aromatic carbonates are conventionally prepared by phosgenation of phenol and phosgene in the presence of an alkali. However, this method uses poisonous phosgene and a neutral salt generated as a by-product must be treated.

In order to solve such disadvantages, transesterification of phenol and aliphatic carbonate such as dimethyl carbonate to produce aromatic carbonate has been developed. The transesterification is generally conducted in the presence of a catalyst, for example, PbO, $TiX_4$ (X=alkoxy or aryloxy group), $SnR_2(OPh)_2$ (R=alkyl group), and the like. PbO has high stability but low catalytic activity, resulting in a significantly low reaction rate. $TiX_4$ and $SnR_2(OPh)_2$ have a higher activity than PbO, but have inadequate stability and generate a substantial amount of ether as a by-product.

Further, a method of preparing aromatic carbonate through carbonylation of an aromatic hydroxyl compound using carbon monoxide and oxygen has been developed. However, since such synthesis using carbon monoxide as a reactant has a remarkably low reactivity and requires a high-pressure reactor, it has limited commercialization potential.

Thus, there is a need for a method for stably preparing aromatic carbonate with high yields using dialkyl carbonate as an initial material instead of carbon monoxide.

SUMMARY OF THE INVENTION

The present invention provides a method of preparing aromatic carbonate with high yields using dialkyl carbonate as a reactant material instead of carbon monoxide. The method can exhibit high catalytic activity to accelerate esterification rate of dialkyl carbonate as compared with a conventional catalytic system, thereby effectively producing diaryl carbonate.

The method includes reacting an aromatic hydroxyl compound and dialkyl carbonate in the presence of at least one type of samarium-containing catalyst represented by the following Formula 1, Formula 2, or a combination thereof:

$SmX_3$            [Formula 1]

wherein each X is the same or different and is independently C1 to C10 alkoxy, C1 to C10 alkyl phenoxy or phenoxy.

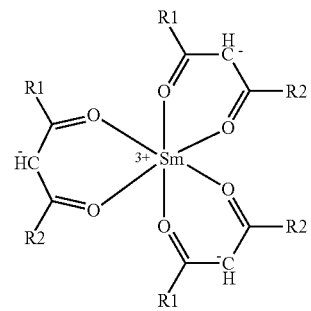

[Formula 2]

wherein R1 and R2 are the same or different and are independently hydrogen or C1 to C6 alkyl.

The catalyst may be used in an amount of about $1 \times 10^{-5}$ to about $5 \times 10^{-1}$ mol based on 1 mole of dialkyl carbonate.

The reaction may be performed at a temperature of about 100 to about 280° C.

The reaction may be performed in a reactor filled with molecular sieves.

The aromatic hydroxyl compound may be represented by Formula 3:

Ar—OH           [Formula 3]

wherein Ar is substituted or non-substituted aryl.

The dialkyl carbonate may be represented by Formula 4:

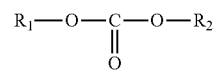

[Formula 4]

wherein $R_1$ and $R_2$ are the same or different and are independently C1 to C6 alkyl group.

The present invention also provides aromatic carbonate synthesized by the above method. The aromatic carbonate is synthesized using at least one type of samarium-containing catalyst represented by Formula 1, Formula 2, or a combination thereof.

The present invention also provides polycarbonate prepared by polymerizing aromatic carbonate prepared by the above method.

BRIEF DESCRIPTION OF THE DRAWING

The above and other aspects, features and advantages of the invention will become apparent from the following detailed description in conjunction with the accompanying drawing, in which:

FIG. 1 illustrates a process of manufacturing polycarbonate according to an exemplary embodiment of the present invention.

DETAILED DESCRIPTION OF THE INVENTION

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements. A method of preparing aromatic carbonate from dialkyl carbonate according to an exemplary embodiment of the invention includes reacting an aromatic hydroxyl compound and dialkyl carbonate in the presence of at least one type of samarium-containing catalyst represented by Formula 1, Formula 2, or a combination thereof.

$$SmX_3, \quad \text{[Formula 1]}$$

wherein each X is the same or different and is independently C1 to C10 alkoxy, C1 to C10 alkyl phenoxy or phenoxy.

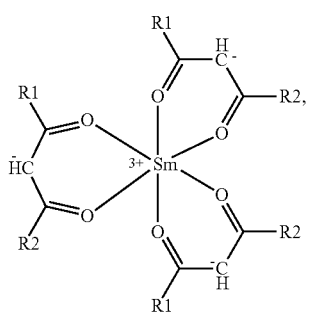

[Formula 2]

wherein R1 and R2 are the same or different and are independently hydrogen or C1 to C6 alkyl. In exemplary embodiments, each R1 and R2 of Formula 2 is hydrogen.

In one embodiment, X may be methoxy, ethoxy, ispropoxy, butoxy, phenoxy, 2,6-di-tert-butyl-4-methylphenoxy, or a combination thereof.

The catalysts represented by Formula 1 Formula 2 may be used as mixtures.

In one embodiment, the catalyst may be used in an amount of about $1 \times 10^{-5}$ to about $5 \times 10^{-1}$ mol, for example about $5 \times 10^{-5}$ to about $5 \times 10^{-2}$ mol, based on 1 mole of dialkyl carbonate. When used in an amount within this range, the catalyst can have excellent efficiency and can be easily recovered.

The aromatic hydroxyl compound may be represented by Formula 3:

$$Ar—OH, \quad \text{[Formula 3]}$$

wherein Ar is substituted or non-substituted aryl.

As used herein, unless a specific definition is otherwise provided, the term "aryl" refers to C6 to C30 aryl, for example C6 to C20 aryl. Exemplary aryl groups include without limitation phenyl and naphthyl groups.

As used herein, unless a specific definition is otherwise provided, the term "substituted" refers to aryl substituted with C1 to C4 alkyl, halogen, C1 to C10 alkoxy, nitro, or cyano, or a combination thereof.

Examples of the aromatic hydroxyl compound may include, but are not limited to, phenol, naphthol, cresol, chlorophenol, C1 to C4 alkylphenol, nitrophenol, cyanophenol, and the like. In exemplary embodiments, the aromatic hydroxyl compound is phenol.

The dialkyl carbonate may be represented by Formula 4:

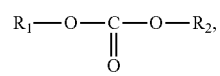

[Formula 4]

wherein $R_1$ and $R_2$ are the same or different and are independently C1 to C6 alkyl.

Examples of dialkyl carbonate may include, but are not limited to, dimethyl carbonate, diethyl carbonate, dipropyl carbonate, dibutyl carbonate, methyl ethyl carbonate, methyl propyl carbonate, and ethyl propyl carbonate. In exemplary embodiments, dimethyl carbonate may be used.

In one embodiment, the reaction may be performed at a temperature of about 100° C. to about 280° C., for example about 120° C. to about 250° C., and as another example about 180° C. to about 240° C. When the reaction is conducted at a temperature within this range, diaryl carbonate can be produced in high yields.

Transesterification may be conducted at a pressure of about 760 mmHg to about 15,000 mmHg, for example about 760 mmHg to about 7,500 mmHg.

The reaction may generally be performed for a time of about 1 second to about 150 minutes, without being limited thereto.

The aromatic carbonate prepared by the above method may be used for polymerization of polycarbonate. Examples of the aromatic carbonate may include, but are not limited to, diphenyl carbonate, ditolyl carbonate, bis(chlorophenyl) carbonate, m-cresyl carbonate, dinaphthyl carbonate, bis(diphenyl) carbonate, and the like, and the aromatic carbonate may be used alone or as a mixture thereof. In exemplary embodiments, diphenyl carbonate may be used.

In one embodiment, the aromatic carbonate obtained by the foregoing method may be transesterified with an aromatic dihydroxy compound, thereby producing polycarbonate.

For example, the aromatic hydroxyl compound and the dialkyl carbonate may be reacted in the presence of at least one type of samarium-containing catalyst represented by Formula 1 or Formula 2 or a combination thereof to prepare aromatic carbonate in a first step. Then, the aromatic carbonate obtained from the first step is transesterified with an aromatic dihydroxy compound to prepare polycarbonate in a second step.

FIG. 1 illustrates a process of preparing polycarbonate according to an exemplary embodiment. As shown in FIG. 1, aromatic hydroxyl compound and dialkyl carbonate may be introduced to a reactor 10 through Line 1 and Line 2, respectively. The reactor 10 may have a catalyst inlet 3 formed at one side thereof. Aromatic carbonate generated in the reactor 10 may be introduced to a reactor 20 through Line 4, and an aromatic hydroxyl compound may be introduced to the reactor 20 through Line 6. The reactor 20 may include a catalyst inlet 7 as necessary. Polycarbonate synthesized in the reactor 20 may be discharged through Line 8. FIG. 1 illustrates the first step and the second step as being performed in separate reactors but the two steps may be performed in the same reactor.

In one embodiment, aromatic carbonate prepared in the first step may be recycled into the reactor 10 through a line 5, thereby improving yield of diaryl carbonate.

The aromatic dihydroxy compound may be represented by Formula 5:

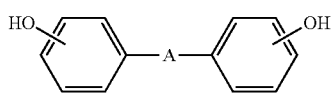

[Formula 5]

wherein A represents a single bond, C1 to C5 alkylene, C1 to C5 alkylidene, C5 to C6 cycloalkylidene, —S—, or $SO_2$.

Examples of the aromatic dihydroxy compound represented by Formula 5 may include without limitation 4,4'-dihydroxydiphenyl, 2,2-bis-(4-hydroxyphenyl)-propane, 2,4-bis-(4-hydroxyphenyl)-2-methylbutane, 1,1-bis-(4-hydroxyphenyl)-cyclohexane, 2,2-bis-(3-chloro-4-hydroxyphenyl)-2-propane, 2,2-bis-(3,5-dichloro-4-hydroxyphenyl)-propane, and the like, and combinations thereof. In exemplary embodiments, the aromatic dihydroxy compound represented by Formula 5 may be 2,2-bis-(4-hydroxyphenyl)-propane (bisphenol A), 2,2-bis-(3,5-dichloro-4-hydroxyphenyl)-propane, 1,1-bis-(4-hydroxyphenyl)-cyclohexane, or a combination thereof.

In one embodiment, the second step may be conducted in the presence of a catalyst. Exemplary catalysts include without limitation including alkali metals, alkaline earth metals, and the like, and mixtures thereof.

In one embodiment, the second step may be conducted under a reduced pressure at a temperature of about 150° C. to about 300° C., for example about 160° C. to about 280° C., and as another example about 190° C. to about 260° C. Within this temperature range, the reaction can be conducted at an appropriate rate and side reactions can be properly decreased.

Further, the second step may be performed under reduced pressure conditions of about 75 torr or less, for example about 30 torr or less, and as another example about 1 torr or less, for at least about 10 minutes, for example about 15 minutes to about 24 hours, and as another example about 15 minutes to about 12 hours in view of reaction rate and decrease in side reaction.

Hereinafter, the constitution and functions of the present invention will be explained in more detail with reference to the following examples. These examples are provided for illustrative purposes only and are not to be in any way construed as limiting the present invention.

Embodiments that are not included herein will be readily recognized and appreciated by those skilled in the art, and an explanation thereof will be omitted herein.

EXAMPLES

Example 1

Phenol (65.88 g, 700 mmol), dimethyl carbonate (31.53 g, 350 mmol) and samarium acetylacetonate hydrate (Sm(acac)$_3$.xH$_2$O) (0.0098 g, 0.022 mmol) as a catalyst are placed in a 200 ml-internal volume autoclave reactor having an external heater, followed by introduction of a nitrogen atmosphere. Then, the reactor is heated to 230° C. and left for 15 minutes, and then cooled using a cooling unit, after which yield and conversion rate are calculated by gas chromatography.

Example 2

The same process as in Example 1 is carried out except that the reactor heated to 230° C. is left for 30 minutes.

Example 3

The same process as in Example 1 is carried out except that the reactor heated to 230° C. is left for 60 minutes.

Example 4

The same process as in Example 1 is carried out except that a cylinder filled with 40 g of molecular sieve (4 Å) is mounted and the reactor heated to 230° C. is left for 30 minutes.

Example 5

The same process as in Example 4 is carried out except that the reactor heated to 230° C. is left for 60 minutes.

Example 6

The same process as in Example 4 is carried out except that the reactor heated to 230° C. is left for 120 minutes.

Example 7

The same process as in Example 1 is carried out except that phenol (32.94 g, 350 mmol) is used.

Comparative Example 1

The same process as in Example 1 is carried out except that n-Bu$_2$SnO is used as a catalyst.

Comparative Example 2

The same process as in Comparative Example 1 is carried out except that the reactor heated to 230° C. is left for 30 minutes.

Comparative Example 3

The same process as in Example 1 is carried out except that n-Bu$_2$Sn(OAc)$_2$ is used as a catalyst.

Comparative Example 4

The same process as in Comparative Example 3 is carried out except that the reactor heated to 230° C. is left for 30 minutes.

Comparative Example 5

The same process as in Example 1 is carried out except that Zr(OBu)$_4$ is used as a catalyst.

Comparative Example 6

The same process as in Comparative Example 5 was carried out except that the reactor heated to 230° C. was left for 30 minutes.

Comparative Example 7

The same process as in Example 6 is carried out except that PbO is used as a catalyst.

Comparative Example 8

The same process as in Example 1 is carried out except that Sm$_2$O$_3$ is used as a catalyst.

TABLE 1

| | | Catalyst | Molecular Sieve | Reaction Temperature (°C.) | Reaction Time (min) | MPC yield[1] (%) | DMC conversion[2] (%) |
|---|---|---|---|---|---|---|---|
| Example | 1 | $Sm(acac)_3 \cdot xH_2O$ | Not filled | 230 | 15 | 6.54 | 7.00 |
| | 2 | $Sm(acac)_3 \cdot xH_2O$ | Not filled | 230 | 30 | 6.78 | 7.73 |
| | 3 | $Sm(acac)_3 \cdot xH_2O$ | Not filled | 230 | 60 | 5.78 | 8.08 |
| | 4 | $Sm(acac)_3 \cdot xH_2O$ | Filled | 230 | 30 | 8.84 | 9.88 |
| | 5 | $Sm(acac)_3 \cdot xH_2O$ | Filled | 230 | 60 | 14.18 | 16.95 |
| | 6 | $Sm(acac)_3 \cdot xH_2O$ | Filled | 230 | 120 | 20.21 | 24.89 |
| | 7 | $Sm(acac)_3 \cdot xH_2O$ | Not filled | 230 | 15 | 5.06 | 5.65 |
| Comparative Example | 1 | $n\text{-}Bu_2SnO$ | Not filled | 230 | 15 | 3.38 | 3.48 |
| | 2 | $n\text{-}Bu_2SnO$ | Not filled | 230 | 30 | 5.58 | 5.70 |
| | 3 | $n\text{-}Bu_2Sn(OAc)_2$ | Not filled | 230 | 15 | 2.37 | 2.46 |
| | 4 | $n\text{-}Bu_2Sn(OAc)_2$ | Not filled | 230 | 30 | 4.67 | 4.78 |
| | 5 | $Zr(OBu)_4$ | Not filled | 230 | 15 | 2.26 | 2.37 |
| | 6 | $Zr(OBu)_4$ | Not filled | 230 | 30 | 4.40 | 4.59 |
| | 7 | PbO | Filled | 230 | 120 | 9.82 | 11.72 |
| | 8 | $Sm_2O_3$ | Not filled | 230 | 15 | 0.35 | 0.40 |

[1] MPC yield = Number of moles of generated methyl phenyl carbonate (MPC)/Number of moles of dimethyl carbonate (DMC) used as reactant × 100
[2] DMC conversion = (Number of moles of generated MPC/Number of moles of diphenyl carbonate + Number of moles of anisole)/Number of moles of DMC used as reactant × 100

As can be seen from Table 1, the products of Examples 1 to 7 have a superior conversion rate to the products of Comparative Example 1 to 8 at the same reaction temperature and time.

Preparation of Polycarbonate

Example 8

196 kg (906 mol) of aromatic carbonate prepared in Example 1, 180 kg (788 mol) of 2,2-bis(4-hydroxyphenyl) propane and 120 ppb (based on 1 mole of BPA) of KOH are sequentially added to a reactor, followed by introduction of a nitrogen atmosphere. The reactor is heated to 160° C. to melt the reactants, and then heated to 190° C. and left for 6 hours. After 6 hours, the reactor is heated to 220° C. and then left at 70 torr for 1 hour. The reactor is heated to 260° C. and left at 20 torr for 1 hour, and then is depressurized to 0.5 torr and left for 1 hour, thereby synthesizing polycarbonate. The produced polycarbonate has a molecular weight (Mw) of 22.0 K.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A method of preparing aromatic carbonate from dialkyl carbonate comprising:
   reacting an aromatic hydroxyl compound and dialkyl carbonate in the presence of at least one type of samarium-containing catalyst represented by Formula 1, Formula 2, or a combination thereof:

$SmX_3$  [Formula 1]

wherein each X is the same or different and is independently C1 to C10 alkyl phenoxy or phenoxy,

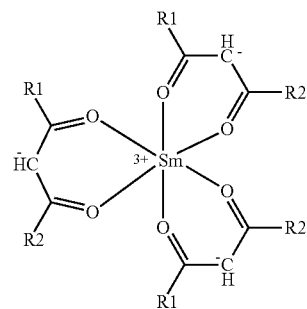

[Formula 2]

wherein R1 and R2 are the same or different and are independently hydrogen or C1 to C6 alkyl.

2. The method of claim 1, wherein said catalyst is used in an amount of about $1 \times 10^{-5}$ to about $5 \times 10^{-1}$ mol based on 1 mole of dialkyl carbonate.

3. The method of claim 1, wherein the reaction is performed at a temperature of about 100 to about 280° C.

4. The method of claim 1, wherein the reaction is performed in a reactor filled with molecular sieves.

5. The method of claim 1, wherein said aromatic hydroxyl compound is represented by Formula 3:

Ar—OH  [Formula 3]

wherein Ar is a substituted or non-substituted aryl.

6. The method of claim 1, wherein said dialkyl carbonate is represented by Formula 4:

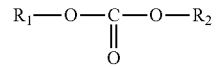

[Formula 4]

wherein $R_1$ and $R_2$ are the same or different and are independently C1 to C6 alkyl.

7. Aromatic carbonate synthesized by the method of any of claim 1.

8. The method of claim 1, wherein the catalyst comprises a samarium-containing catalyst represented by Formula 1.

* * * * *